United States Patent [19]

Jackson et al.

[11] Patent Number: 5,705,652
[45] Date of Patent: Jan. 6, 1998

[54] PREPARATION OF SUBSTITUTED THIAZOLES

[75] Inventors: Arthur Jackson, Washington; Graham Heyes, Durham; James Ian Grayson, Durham; Russell Clarke, Durham, all of England

[73] Assignees: Fine Organics, Ltd., England; Agro-Kanesho Company, Japan

[21] Appl. No.: 711,228

[22] Filed: Sep. 9, 1996

[30] Foreign Application Priority Data

Sep. 14, 1995 [GB] United Kingdom ............... 9518824

[51] Int. Cl.$^6$ ........................... C07D 277/22
[52] U.S. Cl. ........................... 548/202
[58] Field of Search ........................... 548/202

[56] References Cited

U.S. PATENT DOCUMENTS 5,180,833  1/1993  Uneme et al. ............... 548/202

Primary Examiner—Joseph McKane
Attorney, Agent, or Firm—Rodman & Rodman

[57] ABSTRACT

A process for the preparation of a substituted thiazole comprises reacting an isothiocyanate compound of the general formula $$Hal.CH(R_1).CH=C(R_2).NCS$$

in which Hal is a chlorine or bromine atom and $R_1$ and $R_2$ is each a hydrogen atom or an alkyl group containing 1 to 3 carbon atoms, in solution with a chlorinating or brominating agent. The compound 2-chloro-5-(chloromethyl) thiazole, which is an important intermediate in the manufacture of agrochemical and pharmaceutical products, may very advantageously be prepared by this method.

18 Claims, No Drawings

PREPARATION OF SUBSTITUTED THIAZOLES

The present invention is concerned with the preparation of thiazoles which are substituted in the 5 position, namely those having a haloalkyl group in that position. The invention is particularly directed to the preparation of 2-halo-5-(haloalkyl) thiazoles. It may be exemplified by reference to the preparation of 2-chloro-5-(chloromethyl) thiazole.

This latter compound is an important intermediate in the manufacture of agrochemical and pharmaceutical products but there is no method available for its preparation which lends itself to the manufacture of the product on a commercial scale. Such methods as are available entail disadvantages which would render them impractical or uneconomical if attempts were made to adopt them commercially.

By way of example, German Patent Specification No. DE 3631538 describes a method of preparing 2-chloro-5-(chloromethyl) thiazole by chlorination of allyl isothiocyanate. However the reaction requires the use of high temperatures and of a large excess of chlorine or other chlorinating agent. In addition, the desired product is produced with a large number of other substances, from which the desired substituted thiazole is separable only with difficulty.

An alternative method for the preparation of 2-chloro-5-(chloromethyl) thiazole is described in European Patent Specification No. 0446913. According to that method, 2-chloroallyl isothiocyanate is chlorinated using chlorine or another chlorinating agent and gives the desired substituted thiazole in a higher yield than is obtainable by the above-described prior process, without the need for the large excess of chlorinating agent and the high temperatures which together are characteristic of that process. However the allyl isothiocyanate which is the starting material for the improved process is prepared from 2,3- dichloropropene, which latter compound is not readily available. Thus this alternative method, while showing some practical advantages over the first-mentioned method, is not suitable for the manufacture of 2-chloro-5-(chloromethyl) thiazole on a significant scale.

It is therefore an object of the present invention to provide a process for the manufacture of 2-halo-5-(haloalkyl) thiazoles, in particular 2-chloro-5-(chloromethyl) thiazole, by which some at least of the disadvantages of known processes for this purpose are reduced or avoided.

The process according to the present invention comprises reacting an isothiocyanate compound of the general formula Hal.CH($R_1$). CH=C($R_2$).NCS, wherein the symbol Hal represents a chlorine or bromine atom and the symbols $R_1$ and $R_2$ each represents a hydrogen atom or an alkyl group containing from 1 to 3 carbon atoms, in solution with a chlorinating or brominating agent.

The product obtained by the process according to the present invention is a thiazole which has a haloalkyl group in the 5 position and has the general formula

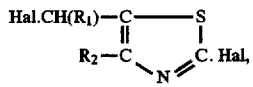

wherein the symbols Hal each represents a chlorine or bromine atom, which may be the same or different, and the symbols $R_1$ and $R_2$ have the meaning given above. Thus where each symbol Hal represents a chlorine atom and where each of the symbols $R_1$ and $R_2$ represents a hydrogen atom, the product obtained is 2-chloro-5-(chloromethyl) thiazole.

The isothiocyanate which is a starting material for the process according to the present invention may be prepared by the method described by K. Schulze et al in Journal fuer Praktische Chemie, 1980, Vol. 322 at pages 629 to 637, wherein a compound of the general formula Hal. CH($R_1$). CH=C($R_2$). Hal wherein the symbols Hal, $R_1$ and $R_2$ have the meanings given above, is reacted with an alkali metal thiocyanate or with ammonium thiocyanate. For example the starting material may be 3-chloroprop-1-enyl isothiocyanate and may be prepared by reacting 1,3-dichloropropene with potassium thiocyanate in this way. 1,3-dichloropropene is a compound which is produced in large quantities as a fumigant and is a readily available and a much cheaper starting material than 2,3-dichloropropene.

The halogenating agent used in the process according to the present invention may be any suitable chlorinating or brominating agent. As chlorinating agent it is particularly preferred to use chlorine itself or sulphuryl chloride. The reaction is preferably carried out at a temperature within the range from –40° C. to +50° C., most preferably within the range from –25° to 0° C.

The reaction is carried out in solution in a suitable solvent. The solvent should preferably be one which does not react with the halogenating agent. For example, when the halogenating agent is a chlorinating agent, suitable solvents include aliphatic or cycloaliphatic hydrocarbons such as hexane or cyclohexane, and chlorinated hydrocarbons, for example dichloromethane, chloroform, 1,2-dichloroethane, 1,1,2-trichloroethane, 1,2,3-trichloropropane, 1,1,2,2-tetrachloroethane and chlorobenzene.

When the isothiocyanate compound which is used as a starting material in the process according to the present invention has been prepared by the method of K. Schulze et al from a di-halo compound as described above, the solvent used in that method may be the same as that used in the subsequent conversion of the isothiocyanate compound to the thiazole, in which case it is not necessary to separate the isothiocyanate compound before carrying out the process of the invention.

The time required for the process of the present invention depends upon the temperature at which it is chosen to carry out the reaction. In general a reaction time of from 1 to 24 hours is preferred.

The substituted thiazole prepared according to the invention may be separated from the reaction mixture by any desired method, for example by distillation or crystallisation. As an alternative, the thiazole may be converted to the form of a salt, for example the hydrochloride, and crystallised from the reaction mixture in that form and in high purity. The salt obtained in this way may be used as such in any further reaction or may be converted to the free base, for example by neutralisation with a base, or by vacuum distillation.

The substituted thiazole obtained by the present process may be further purified if desired, for example by recrystallisation or by distillation.

The invention will now be further described with reference to the following Examples, which illustrate, by way of example, the preparation of 2-chloro-5-(chloromethyl) thiazole or the corresponding hydrochloride salt by the process according to the present invention.

EXAMPLE 1

10 g of 3-chloroprop-1-enyl isothiocyanate prepared by the method of K. Schulze et al described above were dissolved in 70 ml of dichloromethane and a total 15 g of chlorine gas was bubbled into the solution over a period of 2 hours, while the temperature of the solution was maintained at between 10° and 20° C. At the end of this time, GC analysis showed that the isothiocyanate had been consumed.

Removal of the solvent from the resulting reaction mixture, followed by vacuum distillation at 80° C. under 2 mm Hg, yielded 6 g of 2-chloro-5-(chloromethyl) thiazole, in the form of a pale yellow oil which solidified on cooling.

EXAMPLE 2

To a solution of 45 g of 3-chloroprop-1-enyl isothiocyanate in 90 ml of 1,2-dichloroethane, 50.5 g of sulphuryl chloride was added over a period of 10 hours at a temperature of −10° C. The reaction mixture was allowed to warm to 25° C. overnight.

The solution was cooled to −15° C. and the pale yellow solid was isolated by filtration and then washed with hexane. The product was 38.2 g of 2-chloro-5-(chloromethyl) thiazole hydrochloride, of melting point 59°−61° C., being a yield of 61.6%.

EXAMPLE 3

To a solution of 57 g of 3-chloroprop-1-enyl isothiocyanate in 100 ml of dichloromethane, 75.0 g of sulphuryl chloride was added over a period of 10 hours at a temperature from −10° to 0° C. The reaction mixture was allowed to warm to 25° C. overnight and GC analysis showed that the isothiocyanate had been consumed.

Removal of the solvent from the reaction mixture, followed by vacuum distillation at 81° to 83° C. and 2 mm Hg, yielded 30.8 g of a fraction which contained 2-chloro-5-(chloromethyl) thiazole of 75% purity. A portion of this fraction, which was in the form of an oil, was recrystallised from 2 volumes of hexane at −25° C. and gave the pure thiazole in the form of a white solid, of melting point 28°−31° C.

EXAMPLE 4

To a solution of 50 g of 3-chloroprop-1-enyl isothiocyanate in 100 ml of dichloromethane, 54 g of sulphuryl chloride was added over 5 hours at between 0° and −10° C. The reaction mixture was allowed to warm to 25° C. overnight. A further 6 g of sulphuryl chloride was added over 1.5 hours at between 0° and −10° C. and then the reaction mixture was allowed to stand overnight, to complete the reaction. The solution was cooled to −20° C. and the resulting pale yellow solid was isolated by filtration.

The separated product was 42.4 g of 2-chloro-5-(chloromethyl) thiazole hydrochloride, formed from the thiazole itself and by-product hydrogen chloride formed in the reaction. The salt had a melting point of 58°−62° C. and a purity, determined by GC, of 94%.

The mother liquors were evaporated and the residue was dissolved in 30 ml of dichloromethane. On addition of hydrogen chloride gas at −10° C. to the solution, a further 2 g of the thiazole hydrochloride salt was precipitated. The precipitated salt was separated by filtration and had a melting point of 61°−63° C.

EXAMPLE 5

A solution of 277.7 g of 3-chloroprop-2-enyl thiocyanate in 1,1,2,2-tetrachloroethane (1600 ml) was prepared from 1-3-dichloropropene by the above-described method of K. Schulze et al. The solution was heated to 120° C. and held at this temperature for 5 hours. GC analysis showed complete conversion of this thiocyanate to 3-chloroprop-1-enyl isothiocyanate.

The solution was filtered to remove insoluble by-products and then cooled to between 0° and −10° C. Sulphuryl chloride (283 g) was added to the solution at this temperature over a period of 10 to 12 hours and then the reaction mixture was held at this temperature for a further 1 hour, after which time the reaction was complete.

The reaction mixture was fractionally distilled and gave a main fraction of 235 g, containing 57% of 2-chloro-5-(chloromethyl) thiazole and 36% of residual 1,1,2,2-tetrachloroethane. The crude distilled product was dissolved in 470 ml hexane and cooled to −25° C. to crystallise the thiazole. 93 g of white crystalline 2-chloro-5-(chloromethyl) thiazole of purity 98% and melting point 27°−30° C. was obtained. The overall yield based on 3-chloroprop-2-enyl thiocyanate was 33%.

EXAMPLE 6

To a solution of 45 g of 3-chloroprop-1-enyl isothiocyanate in 90 ml of 1,2-dichloroethane, 50.5 g of sulphuryl chloride was added over 10 hours at −10° C. The reaction mixture was allowed to warm to 25° C. overnight, to complete the reaction. The solution was cooled to −15° C. and the product, a pale yellow solid, was isolated by filtration and washed with hexane. 38.2 g of 2-chloro-5-(chloromethyl) thiazole hydrochloride was thus obtained, having a melting point of 59°−61° C. and being a yield of 61.6%.

EXAMPLE 7

A solution of 240 g of 3-chloroprop-2-enyl thiocyanate in 1400 g of 1,1,2-trichloroethane was held at 110° C. for 18 hours. GC analysis showed complete conversion to the isothiocyanate. The solution was filtered to remove insoluble by-products and then cooled to 0° C. 223 g of sulphuryl chloride was added at this temperature over a period of 10 hours and the reaction mixture was held at this temperature for a further 1 hour. The reaction mixture was fractionally distilled and gave a main fraction containing 96.2 g of 2-chloro-5-(chloromethyl) thiazole, being a yield of 32% on the original thiocyanate.

EXAMPLE 8

The reaction was carried out as in Example 7, except that the 1,1,2-trichloroethane solvent was replaced by the same weight of chlorobenzene. After the chlorination with sulphuryl chloride, the chlorobenzene was removed by evaporation under vacuum and the residue was dissolved in dichloromethane and saturated with gaseous hydrogen chloride. A 23% yield of 2-chloro-5-(chloromethyl) thiazole hydrochloride was isolated as a pale yellow solid.

EXAMPLE 9

A solution of 50 g of 3-chloroprop-2-enyl thiocyanate in 300 g of 1,2,3-trichloropropane was held at 150° C. for 4 hours after which GC analysis showed complete conversion of the thiocyanate to isothiocyanate. The solution was filtered to remove insoluble by-products and then cooled to −20° C. At this temperature, a solution of 60 g of sulphuryl chloride in 180 g of dichloromethane was added over a period of 8 hours and the reaction mixture was then warmed to 25° C. Fractional distillation of the reaction mixture gave a main fraction containing 18.6 g of 2-chloro-5-(chloromethyl) thiazole of 85% purity, the remainder being 1,2,3-trichloropropane.

EXAMPLE 10

A solution of 100 g of 3-chloroprop-2-enyl thiocyanate in 600 ml of 1,2-dichloroethane was heated to 110° C. in an autoclave and held at this temperature for 12 hours. The excess pressure was 1.0 bar. The solution was filtered to remove insoluble by-products and the solvent was evaporated, giving a final volume of 300 ml. To this solution 153 g of sulphuryl chloride was added at −20° C. over 18 hours. The reaction mixture was allowed to warm to 20° C. and was then cooled to −20° C. to crystallize the product hydrochloride. The 2-chloro-5-(chloromethyl) thiazole hydrochloride was filtered off as a pale yellow solid and was washed with hexane. The weight of the hydrochloride thus obtained was 102.1 g, being a yield of 66.6%.

As will be apparent from the foregoing Examples, in the case of 2-chloro-5-(chloromethyl) thiazole, the process makes possible the production of the substituted thiazole in good yields by means of a reaction at acceptable temperatures starting from 1,3-dichloropropene, which as already mentioned is a compound which is produced in large quantities as a fumigant and is therefore readily available.

We claim:

1. A process for the preparation of a substituted thiazole, which process comprises reacting an isothiocyanate compound of the general formula $$Hal.CH(R_1).CH=C(R_2).NCS,$$

wherein the symbol Hal represents a chlorine atom or a bromine atom and the symbols $R_1$ and $R_2$ each represents a hydrogen atom or an alkyl group containing from 1 to 3 carbon atoms, in solution, with a chlorinating agent or a brominating agent.

2. A process according to claim 1, wherein the isothiocyanate compound has the general formula $$Hal.CH_2.CH=CH.NCS$$

wherein the symbol Hal represents a chlorine atom or a bromine atom.

3. A process according to claim 2, wherein the isothiocyanate compound is 3-chloroprop-1-enyl isothiocyanate.

4. A process according to claim 1, wherein the isothiocyanate compound had been prepared by reacting a compound of the general formula $$Hal.CH(R_1).CH=C(R_2).Hal,$$

wherein the symbols Hal, $R_1$ and $R_2$ have the meanings given in claim 1, with an alkali metal thiocyanate or with ammonium thiocyanate.

5. A process according to claim 4, wherein said preparation of said isothiocyanate compound is carried out in the same solvent as is used for reacting the resulting isothiocyanate compound with a chlorinating agent or a brominating agent.

6. A process according to claim 5, wherein said solvent is an aliphatic or cycloaliphatic hydrocarbon or a chlorinated hydrocarbon.

7. A process for the preparation of 2-chloro-5-(chloromethyl) thiazole, which process comprises reacting 3-chloroprop-1-enyl isothiocyanate with a chlorinating agent, in solution in a solvent.

8. A process according to claim 7, wherein the solvent is an aliphatic or cycloaliphatic hydrocarbon or a chlorinated hydrocarbon.

9. A process according to claim 8, wherein the solvent is hexane or cyclohexane.

10. A process according to claim 8, wherein the solvent is a chlorinated hydrocarbon selected from the group comprising dichloromethane, chloroform, 1,2-dichloroethane, 1,1,2-trichloroethane, 1,2,3-trichloropropane, 1,1,2,2-tetrachloroethane and chlorobenzene.

11. A process according to claim 7, wherein the chlorinating agent is chlorine or sulphuryl chloride.

12. A process for the preparation of 2-chloro-5-(chloromethyl) thiazole, which process comprises reacting 3-chloroprop-1-enyl isothiocyanate with sulphuryl chloride, the reaction being carried out in a chlorinated hydrocarbon solvent selected from the group comprising dichloromethane, chloroform, 1,2-dichloroethane, 1,1,2-trichloroethane, 1,2,3-trichloropropane, 1,1,2,2-tetrachloroethane and chlorobenzene.

13. A process according to claim 12, wherein said reaction is carried out at a temperature lying within the range from −40° C. to +50° C.

14. A process according to claim 13, wherein said reaction temperature lies within the range from −25° C. to 0° C.

15. A process according to claim 12, wherein the thiazole so prepared is separated from the reaction mixture by distillation or crystallisation.

16. A process according to claim 12, wherein the thiazole so prepared is converted to a salt and separated in that form by crystallisation.

17. A process according to claim 12, wherein the thiazole so prepared is converted to 2-chloro-5-(chloromethyl) thiazole hydrochloride and separated in the form of that hydrochloride.

18. A process according to claim 1, wherein the substituted thiazole has the general formula $$Hal.CH(R_1)-C\overset{\displaystyle S}{\underset{\displaystyle \underset{N}{\|}}{\|}}C.Hal$$
$$R_2-C$$

wherein the symbols Hal, $R_1$ and $R_2$ have the meanings given in claim 1.

* * * * *